United States Patent [19]
Thurman et al.

[11] Patent Number: 5,180,847
[45] Date of Patent: Jan. 19, 1993

[54] PROCESSES FOR PREPARING 2,2,4-TRIMETHYL-1,3-PENTANEDIOL DERIVATIVES

[75] Inventors: Laurance R. Thurman, Clute; James B. Harris, Pearland, both of Tex.

[73] Assignee: BASF Corporation, Parsippany, N.J.

[21] Appl. No.: 656,789

[22] Filed: Feb. 15, 1991

[51] Int. Cl.$^5$ .................... C07C 67/00; C07C 69/28
[52] U.S. Cl. .................... 560/238; 560/240
[58] Field of Search .................... 560/238, 240

[56] References Cited

U.S. PATENT DOCUMENTS

| | | | |
|---|---|---|---|
| 3,091,632 | 5/1963 | Hagemeyer et al. | 560/238 X |
| 3,291,821 | 12/1966 | Perry et al. | 560/238 |
| 3,442,931 | 5/1969 | Duke et al. | 560/238 X |
| 3,475,343 | 10/1969 | Kusama et al. | 252/364 |
| 3,703,541 | 11/1972 | Takasu et al. | 560/238 |
| 3,718,689 | 2/1973 | McCain et al. | 560/238 |
| 4,225,726 | 9/1980 | Morris et al. | 560/238 |
| 4,273,934 | 6/1981 | Merger et al. | 560/238 |
| 4,883,906 | 11/1989 | Argyropoulos et al. | 560/238 |

*Primary Examiner*—Arthur C. Prescott
*Assistant Examiner*—V. Garner

[57] ABSTRACT

A preferred process for producing 3-hydroxy-2,2,4-trimethylpentyl isobutyrate is described. The spent aqueous phase from an alkali metal hydroxide-catalyzed isobutyraldehyde condensation is concentrated in alkali metal isobutyrate salt, and the concentrated medium is introduced into a subsequent condensation to advantageously modify the isobutyraldehyde reaction. Increased conversions and productivities can thus be achieved. Preferred continuous processes, as well as preferred processes of controlled reaction duration and reactant/catalyst/salt ratios are also described. Further described is a preferred process for producing the diisobutyrate ester of 2,2,4-trimethyl-1,3-pentanediol, which in a preferred mode also achieves a desirable coproduction of the diol and its monoisobutyrate ester.

34 Claims, 2 Drawing Sheets

PROCESSES FOR PREPARING 2,2,4-TRIMETHYL-1,3-PENTANEDIOL DERIVATIVES

BACKGROUND

This invention relates to processes for preparing 2,2,4-trimethyl-1,3-pentanediol and derivatives thereof including its mono- and diisobutyrate esters. More particularly, the invention relates to alkali metal hydroxide catalyzed processes for such preparation which are unexpectedly and advantageously modified by the presence of alkali metal isobutyrate salts.

By way of further background, 2,2,4-trimethyl-1,3-pentanediol and its derivatives, including for example its mono- and diisobutyrate esters, have proven to be highly useful materials. For instance, they have been used as or as intermediates to plasticizers, pesticides, polyester resins, lubricants, printing inks, etc. Quite naturally, therefore, much study has focussed upon achieving and improving upon processes for the production of these chemicals.

For example, the base-catalyzed condensation of isobutyraldehyde to 2,2,4-trimethyl-1,3-pentanediol and corresponding esters, and particularly to its monoisobutyrate ester (3-hydroxy-2,2,4-trimethylpentyl isobutyrate, sometimes referred to herein as "the monoester"), has been the subject of continuing study throughout the years. Such studies have been reported extensively in the patent and other literature. For example, U.S. Pat. No. 3,091,632 issued to Hagemeyer et al. in 1963 reports the use of alkali metal alkoxide catalyst, under dry, acid free conditions, to catalyze the condensation of aldehydes such as isobutyraldehyde to glycol monoesters. The condensations are said to occur at a temperature of 65° C. to 105° C., a catalyst concentration 0.05 to 2 weight percent based on the aldehyde feed, and a residence time within the reaction zone in the range of 0.25 to 3 hours.

U.S. Pat. No. 3,291,821 to Perry et al. discloses aldehyde condensations catalyzed by alkali metal hydroxides or alkaline earth metal hydroxides. An aqueous solution of the base is intimately contacted with the aldehyde for a period of about 15 minutes to 2 hours at a temperature of about 50° C. to 125° C. The alkali metal hydroxide, sodium hydroxide, is preferred, with a 10% by weight aqueous solution typically being used at an organic to aqueous phase ratio of 85:15 to 75:25. The mixing of the aqueous and organic phases is accomplished by directing them against a baffle plate disposed within a reactor tank. The Perry et al. patent also describes recycling a portion of the spent catalyst solution directly back into the catalyst feed. In so doing, Perry et al. note that recycling the catalyst solution leads to a build up of water-soluble organic acid salts in the aqueous catalyst solution, and caution that "these salts inhibit the formation of the desired glycol monoester and the salt concentration must therefore be controlled." Perry et al. thus direct that the salt concentration in the catalyst solution be kept at less than 10% of the solution by weight and preferably less than 5 weight %. Following this work, U.S. Pat. No. 3,442,931 to Duke and Perry described a mixed, trimeric aldehyde condensation in which formaldehyde and aldehydes having only one alpha-hydrogen atom were contacted with a strongly basic catalyst at a temperature below 50° C. Reaction times described in the examples are typically 3 hours or more, with other features of the reaction, including catalyst recycle and cautioned control of salt build up, being similar to those set forth in the above-described Perry et al. '821 patent After this earlier work in the 1960's, researchers continued to study the aldehyde condensation reaction and set out to try to maximize productivity while maintaining acceptable monoester selectivities and yields. For example, U.S. Pat. No. 3,718,689 issued to McCain et al. in 1973 describes a process for producing high ratios of hydroxyalkyl alkanoate product with relation to alkanediol byproduct. The described process includes continuously subjecting, in a longitudinal flow zone, an intimate mixture containing aldehyde and smaller amounts of a relatively concentrated aqueous basic solution, e.g. aqueous alkali metal or alkaline earth metal hydroxides. Again, the alkali metal hydroxide, sodium hydroxide, is the preferred catalyst. McCain et al. state that residence periods up to about 2 hours give satisfactory results, and indicate that marked increases in productivity are obtained by maintaining a maximum residence period of up to approximately ten minutes. McCain et al. describe no attempt to recycle catalyst solutions, rather directing that the spent aqueous stream containing dissolved salts be removed and discarded.

Despite varying catalysts described in early and more recent literature, alkali metal hydroxides such as sodium hydroxide have remained the preferred catalysts in the field and industry to date. For example, more recently, U.S. Pat. No. 4,883,906 issued to Argyropoulos et al. in 1989 describes a process in which sodium hydroxide is the preferred catalyst. This process involves distilling the reaction product immediately after leaving the reactor and before it has cooled or been contacted with any added water. The patent states that this step significantly reduces byproducts and simplifies purification of the product. The patent also indicates the need to carefully control this initial distillation to prevent or minimize decomposition of the desired monoester product to diol and diester byproducts.

As to other catalysts which have been described for aldehyde condensations, U.S. Pat. No. 3,475,343 to Kusama et al. describes a process which forms a mixture of aliphatic carboxylic acid esters by subjecting a mixture of saturated aliphatic aldehydes or 4-alkoxy substitutes thereof to condensation in the presence of aluminum alcoholate catalyst. U.S. Pat. No. 4,273,934 to Merger et al. describes preparation of 3-hydroxy-2,2,4-trimethylpentyl isobutyrate using an alkaline earth metal hydroxide and carboxylic acids or the corresponding alkali metal or alkaline earth metal salts. U.S. Pat. No. 3,703,541 describes isobutyraldehyde condensation to the monoester in the presence of an alkali metal salt of a monohydric or polyhydric phenol; and, U.S. Pat. No. 4,225,726 describes condensations of aldehydes in the presence of tin metal or tin oxide catalyst.

In light of this extensive background, there remains a need for improved processes employing the preferred alkali metal hydroxide catalysts which can provide even greater monoester productivities while maintaining good yields and selectivities. Additionally, despite their frequent characterization as "byproducts", the diol and diester and other derivative products also enjoy demand in commerce. Accordingly, there is a need for processes which can effectively be used to control the relative amounts of the monoester, diol and diester products, to meet current market demands. The applicants' invention addresses these and other needs in its various embodiments, and provides surprising processes in which condensation reactions are highly and unexpectedly modified by the presence of alkalai metal isobutyrate salts.

SUMMARY OF THE INVENTION

In brief summary, one preferred embodiment of the invention relates to a process for producing 3-hydroxy-2,2,4-trimethylpentyl isobutyrate. Isobutyraldehyde is reacted in the presence of an alkali metal hydroxide to produce a reacted medium containing said isobutyrate and an alkali metal isobutyrate salt. An aqueous medium containing the alkali metal isobutyrate salt is separated from the reacted medium. Water is removed from the aqueous medium to concentrate it in the alkali metal isobutyrate salt; and, the concentrated alkali metal isobutyrate salt medium is introduced into a subsequent reacting step to increase the rate of the reacting. Surprisingly, the applicants have discovered that the alkali metal hydroxide-catalyzed reaction of the aldehyde occurs more rapidly in the presence of the isobutyrate salt. Thus, provided in this first-described preferred embodiment is a featured process in which the spent aqueous phase containing the isobutyrate salt is concentrated in the salt and used to enhance the condensation reaction.

Capitalizing on the unexpected rate enhancement provided by the isobutyrate salt, the invention provides in another preferred embodiment a process for producing 3-hydroxy-2,2,4-trimethylpentyl isobutyrate which includes reacting isobutyraldehyde in the presence of an alkali metal isobutyrate salt and an alkali metal hydroxide for a duration of about 0.5 to about 10 minutes. Another preferred embodiment of the invention provides a process for producing 3-hydroxy-2,2,4-trimethylpentyl isobutyrate which includes reacting isobutyraldehyde in the presence of about 0.5 to about 5 weight percent, based on the isobutyraldehyde, of an aqueous phase containing at least about 15 weight percent sodium hydroxide and at least about 12.5 weight percent sodium isobutyrate.

Still another preferred embodiment of this invention relates to a process for the production of the diisobutyrate ester of 2,2,4-trimethyl-1,3-pentanediol. This preferred process includes the step of reacting 3-hydroxy-2,2,4-trimethylpentyl isobutyrate in the presence of an alkalai metal isobutyrate for a time and at a temperature sufficient to obtain a reaction product containing at least about 10% by weight of the diisobutyrate ester produced. In preferred modes, this preferred process is used to achieve controlled coproduction of the diester, the diol and the monoester.

Additional preferred features of the the invention, as well as objects and advantages thereof, will be apparent upon reviewing the following description and appended claims.

DESCRIPTION OF THE PREFERRED EMBODIMENTS

Figure 1:
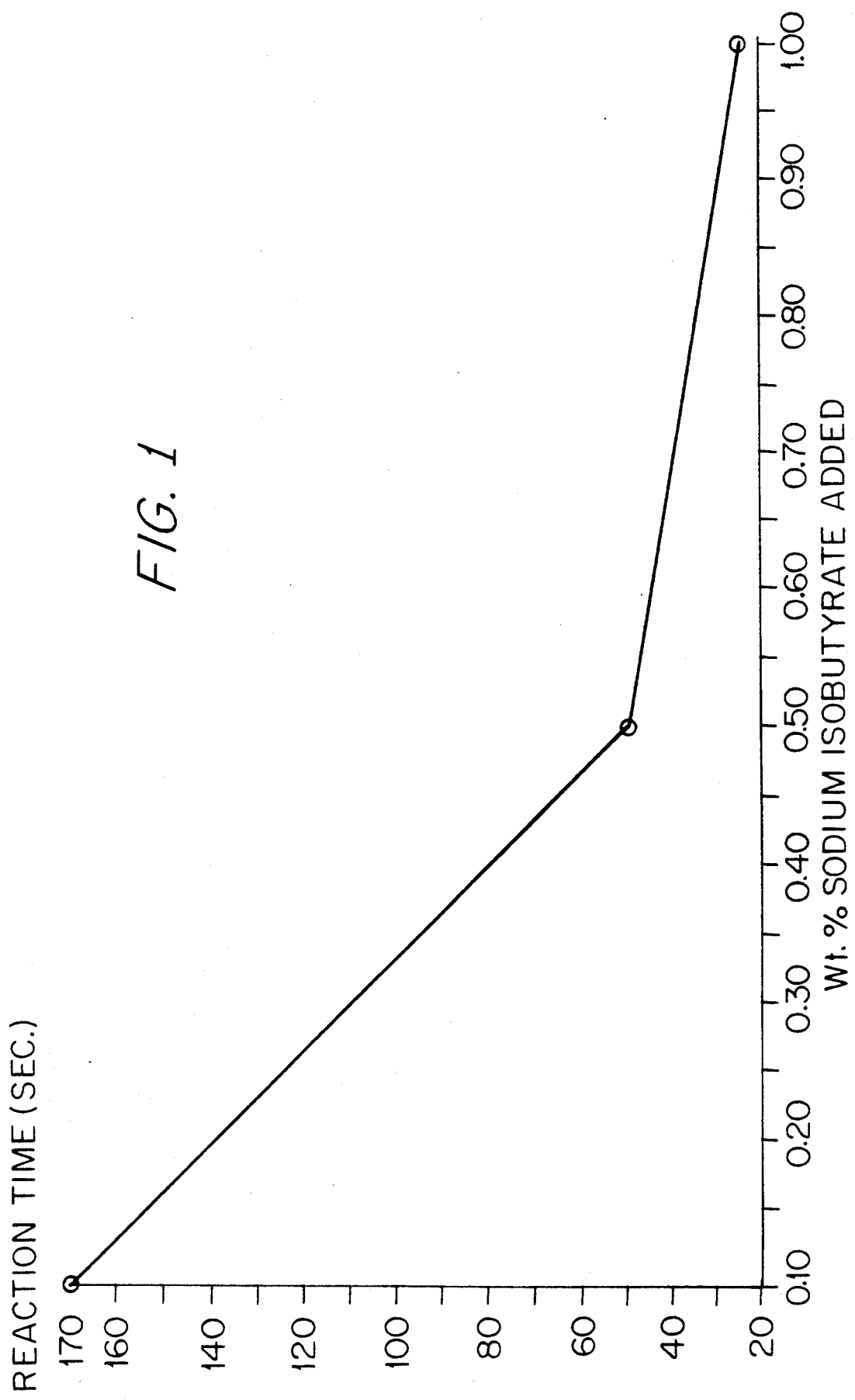
FIG. 1 is a graphical representation of reaction time (for a sodium hydroxide-catalyzed condensation of isobutyraldehyde) versus the amount of sodium isobutyrate added.

For the purposes of promoting an understanding of the principles of the invention, reference will now be made to certain embodiments and specific language will be used to describe them. It will nevertheless be understood that no limitation of the scope of the invention is thereby intended, such alterations, and further modifications and applications of the principles of the invention being contemplated as would normally occur to one skilled in the art to which the invention relates.

As is well known, the synthesis of 3-hydroxy-2,2,4-trimethylpentyl isobutyrate can be achieved by a self-polymerization of isobutyraldehyde in the presence of alkali metal hydroxide, e.g. NaOH, to form initially a C-8 aldol condensation product. This aldol product reacts with monomeric isobutyraldehyde to form in competing reactions the monoester (by Tishcenko reaction), and the isobutyraldehyde trimer aldoxane. The aldoxane during the course of the process sequence is typically decomposed to yield isobutyraldehyde monomer. Typically, primary coproducts from such condensations occurring in the organic phase are 2,2,4-trimethyl-1,3-pentanediol ("the diol") and its diisobutyrate ester ("the diester").

As stated above, one preferred embodiment of this invention relates to a process for producing the monoester in which spent aqueous catalyst medium from a previous condensation reaction is concentrated in the alkali metal isobutyrate salt present. This concentrated isobutyrate salt medium is introduced into a subsequent reacting step to increase the rate of the reacting. It has been discovered that rate of the aldehyde condensation reaction can thereby unexpectedly be enhanced. Further, it has surprisingly been discovered that this presence of alkali metal isobutyrate salt during the reacting suppresses the formation of the diol and can improve the overall monoester product purity.

The isobutyraldehyde used can contain water up to its solubility limit, but preferably contains 5 weight percent water or less, based on the isobutyraldehyde. It is preferred that the isobutyraldehyde contain no or relatively little acid, and therefore water-containing material should be protected from the atmosphere as necessary to prevent significant acid buildup.

As already indicated, the catalyst is an alkali metal hydroxide, desirably used in an amount of about 0.1 to about 5 moles per 100 moles of isobutyraldehyde, more preferably about 0.75 to about 1.25 moles per 100 moles of isobutyraldehyde. To date, sodium hydroxide has been the most preferred alkali metal hydroxide. In preferred processes, the catalyst has been added as an aqueous stream containing at least about 30 weight % sodium hydroxide, more preferably at least about 40-50%. This aqueous stream is advantageously introduced in an amount of about 0.25 to about 5 weight percent, and more preferably about 1 weight percent, relative to the isobutyraldehyde present during the reacting.

After the reacting step, the spent aqueous medium contains alkali metal isobutyrate salt. In accordance with this embodiment of the invention, this aqueous medium is separated from the organic phase by decantation or any other suitable means. Water is then removed from the aqueous medium to increase the concentration of the isobutyrate salt therein. This water removal is preferably accomplished by distillation, although other conventional methods can be used without departing from the scope of the invention. It is also preferred that the aqueous medium be concentrated so as to contain at least about 12.5 weight % of the isobutyrate salt, more preferably at least about 20% by weight, and most preferably at least about 30% by weight of the salt, e.g. 40–60% or more.

After concentration, the aqueous medium is introduced into another reacting step along with the isobutyraldehyde and the alkali metal hydroxide. In this regard, the concentrated salt medium is advantageously introduced in an amount of about 0.1 to about 5 weight percent, and more preferably about 1 weight percent, relative to the isobutyraldehyde present during the reacting. As Example 1 demonstrates, the presence of the alkali metal isobutyrate during the reacting significantly enhances the rate of the aldehyde reaction. Accordingly, higher conversions can be obtained in the same or lower reaction times than if the salt was not present, and consequently greater productivities can be achieved. Further, as also discussed in Example 1, the presence of the isobutyrate salt during the reaction unexpectedly supresses formation of the diol. Moreover, these advantages can be obtained while maintaining good yields and without significant effect on monoester selectivity. In this regard, preferred reactions have achieved monoester yields of at least about 60%, and demonstrate superior selectivities, desirably producing monoester to diol in a molar ratio of at least abut 6 to 1.

The condensation reaction is suitably conducted at a temperature of about 60° to about 120° C., more preferably about 75° to about 100° C., and most preferably about 80° to about 90° C. The pressure during the reacting has not proven critical to date, with atmospheric or superatmospheric pressures being suitable. It is preferred however that at least sufficient pressure be maintained during the reacting to minimize vaporization of the isubutyraldehyde, e.g. about 70 to 100 psig in the applicants' work so far.

The condensation reaction is suitably conducted over a period up to about 2 hours. However, as the applicants have discovered, the presence of the alkali metal isobutyrate significantly enhances the reaction rate. Thus, advantageous reactions having good conversions can be and are preferably conducted with reaction times up to about 10 minutes, e.g. about 0.5 to about 10 minutes, with preferred reaction times being about 1 to about 8 minutes, more preferably about 3 to about 6 minutes. Further, the reaction is desirably conducted in a tubular flow reactor, although other reactor designs are suitable. The preferred tubular flow reactor can be coiled or straight tubing, for example, and preferably contains means for agitating the reaction mixture as it passes through the reactor. In this regard, it is preferred that the reactor have a plurality of mixing elements therein, for instance up to 5 and even 10 or more mixing elements as illustrated by the static mixer device employed in applicants' work reported in the Example 2 below. This achieves advantageous intimate mixing of the aqueous and organic phases, and provides increased conversions over time. In a preferred aspect, the synthesis is run in a continuous fashion from reaction to final distillation, for example as also illustrated by the process specifically described in Example 2 below. Preferred of such processes have achieved the monoester in purities of 90% or more.

As indicated above, another preferred embodiment of the invention includes a process for producing 3-hydroxy-2,2,4-trimethylpentyl isobutyrate in which the duration of the reaction is controlled. The isobutyraldehyde is reacted in the presence of an alkali metal isobutyrate salt and an alkali metal hydroxide for a duration of about 0.5 to about 10 minutes. This embodiment accordingly capitalizes on the unexpected rate enhancement by the isobutyrate salt, and can provide high productivities as well as good selectivities and yields. Another preferred embodiment of the invention involves a process for producing the monoester which includes reacting isobutyraldehyde in the presence of controlled amounts of an aqueous phase containing alkali metal isobutyrate salt and alkali metal hydroxides in specified proportions. In this regard, isobutyraldehyde is reacted in the presence of about 0.5 to about 5 weight percent, based on the isobutyraldehyde, of an aqueous phase containing at least about 15 weight percent sodium hydroxide and at least about 12.5 weight percent sodium isobutyrate, more preferably at least about 30 weight % sodium hydroxide and at least about 20 weight % sodium isobutyrate. Additional preferred features of these two embodiments are similar to those set forth for the first-described embodiment above.

As already indicated, still another preferred embodiment of this invention relates to the applicants' discovery that heating 3-hydroxy-2,2,4-trimethylpentyl isobutyrate in the presence of an alkali metal isobutyrate salt unexpectedly yields large amounts of the diester product. Accordingly, this embodiment is directed to a process for producing the diisobutyrate ester of 2,2,4-trimethyl-1,3-pentanediol, which includes the step of reacting 3-hydroxy-2,2,4-trimethylpentyl isobutyrate in the presence of an alkalai metal isobutyrate for a time and at a temperature sufficient to obtain a reaction product comprised at least about 10% by weight of the produced diisobutyrate ester. The monoisobutyrate starting material can be obtained commercially or synthesized by procedures well known to those skilled in this field. In addition to the monoester, the starting material may already contain some diester product as well as some diol, for example present as coproducts in a previous monoester synthesis. Accordingly, for purposes of the description herein, any diester already present in the starting material is excluded from the calculation of the percent by weight diester in the final reaction product. In this regard, as indicated, the reaction is conducted under conditions so as to achieve at least about 10% by weight of the formed diester product. The time and temperature required to achieve this result are interdependent. Those practiced in this area will of course be able to control these conditions to achieve the beneficially diester-enriched product as described herein.

In a preferred mode, the process of this embodiment is used to achieve the controlled coproduction of the diol, monoester and diester. This unique process can be achieved, for example, by refluxing, for instance distilling the crude product of an alkali metal hydroxide-catalyzed condensation of isobutyraldehyde while still containing a significant amount of alkali metal (e.g. sodium) isobutyrate produced during the condensation, desirably at least about 0.1 weight percent and more desirably 0.5 weight percent or more. One such representative process is set forth in Example 3 below. A monoester, diol and isobutyraldehyde distillation feed contained only minor amounts (approx. 0.3 wt. %) of the diester, and 0.5 wt. % sodium isobutyrate. After the distillation was stopped, it was discovered that the diester accounted for about 36% of the total product (tops and bottoms). Further, the diester detected in the bottoms rose sharply after about 15% of the pot charge had been removed, with the bottoms being comprised about 70% of the diester after about 30% of the charge was removed, and about 78 weight % by the time about 55% of the charge was removed. Upon final analysis, the feed streams from the distillation column showed an effective coproduction of the desired products, containing about 36% diester, 41% monoester and 28% diol.

Of course, the relative amounts of these products obtained in the final product stream are interdependent, and can be controlled by varying the time and/or temperature of the reacting. For example, reaction conditions adjusted to increase diester formation (e.g. conducting longer and more complete distillations) will typically also result in an increase in diol formation. In this regard, the diester can desirably constitute from about 10 up to about 50 wt. % or more of the total reaction product, with the diol being similarly achievable in range of about 10% to about 50% by weight or more. The amount of monoester remaining in the final product will, of course, be inversely proportional to the amounts of the diol and diester produced, but in preferred runs has constituted about 10% to about 50% by weight or more of the total reaction product. The temperature during this reacting can vary, e.g. about 130° or above and preferably about 140° to 210° C., more preferably about 150° to 185° C. The duration, likewise, can vary, e.g. up to 72 hours, more preferably about 0.5 to 24 hours. Column pressures of preferred reactions have been about 20mm Hg. As stated, one preferred mode of carrying out this reacting is to simply distill the reaction mixture for a period necessary to obtain the desired product composition.

In a preferred aspect of the invention, reaction product from a process such as those described in the embodiments above (isobutyrate salt added during the condensation reaction) is distilled without washing, or completely washing the sodium isobutyrate, therefrom. A controlled coproduction of the diol and the mono- and diisobutyrate esters can thereby be achieved. Further, a particularly preferred process is achieved wherein a continuous process, such as that described in Example 2 below, is run only without or without complete salt wash prior to distillation at temperatures leading to the formation of substantial amounts of diester. A highly advantageous continuous process can thus be run to obtain final product streams with controlled levels of these three desired products. As such, additional preferred features of this embodiment are similar to those described in the embodiments above, only advantageously controlling the amount of salt during distillation, as well as the extent of distillation.

All publications cited or referred to in this application are hereby incorporated by reference in all aspects relevant and material to the invention.

In order to promote a further understanding of the invention and its preferred features and advantages, the following specific Examples are provided. It will be understood that these Examples are illustrative and not restrictive in character, and that all changes and modifications that come within the spirit of the invention are desired to be protected.

EXAMPLE 1

Reaction Enhancement With Alkali Metal Isobutyrate Salt

In a series of experiments, the ability of sodium isobutyrate salt to enhance the aldehyde condensation reaction was studied. For the testing, sodium isobutyrate was added in varying amounts to an isobutyraldehyde feed into a mixed vessel. The salt was added in amounts to achieve from 0.1 to 1 weight % salt relative to the isobutyraldehyde in consecutive runs. A 1% sodium hydroxide solution was also fed into the vessel, to achieve a sodium hydroxide to isobutyraldehyde molar ratio of 1 to 100. The salt for these tests was obtained by water extracting it from previously prepared reaction products, and then vacuum drying the extract. The results of this testing are set forth in FIG. 1, which is a graphical representation of reaction time versus amount of added salt. As can be seen, an increase from 0.1 to 1.0 weight % sodium isobutyrate salt (relative to isobutyraldehyde) before the addition of the NaOH dramatically reduced the reaction time from 170 to 25 seconds. In these experiments, the reaction time was considered to be the amount of time elapsed before the test solution began to reflux after the NaOH had been added. Following up on this work, additional testing and product analysis indicated that in continuous syntheses in tubular flow reactors, conversions of isobutyraldehyde starting material could be significantly increased by the introduction of a feed concentrated in isobutyraldehyde salt into the reaction zone. Further, these significant increases in conversion were accompanied by suppression of diol formation and good monoester yields and selectivities. Thus, processes having improved monoester productivity can be achieved in accordance with the invention. Further, to confirm the surprising effect of the salt, purified sodium isobutyrate was obtained from a commercial source and used in analogous testing in place of the salts obtained from previous condensations. Unexpected reaction enhancement and modification was again experienced, thus evidencing the surprising effects owing to the isobutyrate salt.

EXAMPLE 2

Continuous Synthesis

Figure 2:
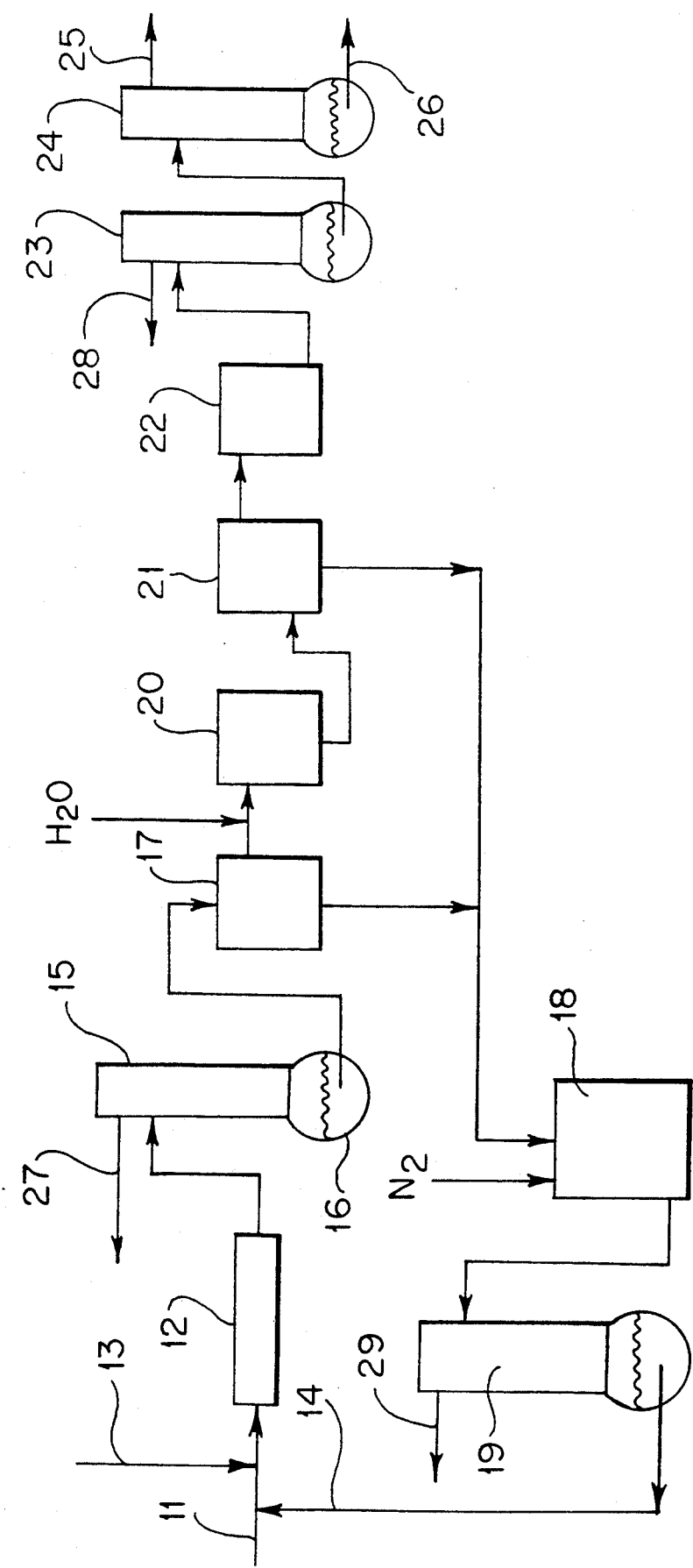
FIG. 2 is a schematic representation of a preferred continuous process for producing 3-hydroxy-2,2,4-trimethylpentyl isobutyrate in accordance with the invention.

Referring now to FIG. 2, a preferred reaction is conducted in a continuous manner from synthesis to final distillation without interruption. This mode of operation minimizes aging of crude monoester prior to distillation. In the synthesis, isobutyraldehyde is continuously fed through line 11 to a static mixer 12 containing ten mixing elements. One such suitable static mixer is available from Koch Engineering of Wichita, Kansas. This stainless steel static mixer is approximately six inches long and has a reaction volume of approximately 20 cm³.

Tubing without mixing, for example coiled tubing, can also be used to provide a reaction zone. However, the static mixer was found to be highly preferred as it provided increased conversions and monoester yields and selectivities. In fact, the results from static mixer testing by applicants indicate the reaction is largely complete within 40 seconds or even less in many cases.

NaOH and sodium isobutyrate salt solutions were fed to the mixer 12 through lines 13 and 14 to act as catalyst and reaction enhancer, respectively. The mixer 12 was operated at 80 to 90 psig and at a temperature of approximately 90° C. The static mixer 12 provided thorough blending of the reactants and sufficient pressure was maintained to minimize isobutyraldehyde vaporization. The synthesis product was forwarded to distillation column 15 having a nitrogen purge. Unreacted isobutyraldehyde was stripped overhead, aldoxanes formed in synthesis were converted back to isobutyraldehyde, and sodium isobutyrate salts formed in synthesis were solubilized to prevent salting out. The overhead temperature of column 15 operated to 70–75° C. and the bottom at 95° C. Column pressure was about 20mm Hg. The organic phase of the distillate was recycled via line 27 to the isobutyraldehyde feed tank and the bottoms were collected into kettle 16. The bottoms from kettle 16 containing the crude monoester product were forwarded to vessel 17. The underflow, containing aqueous sodium salts, was forwarded to nitrogen purged tank 18 and then to packed distillation column 19. The organic overflow was washed with water and forwarded to vessel 20. In one preferred mode, another static mixer is used to agitate the water and product stream at this point to achieve a highly effective wash. The effluent from vessel 20 was sent to tank 21. The aqueous underflow from tank 21 was sent to tank 18, and the organic overflow from tank 21 was forwarded through tank 22 to the final distillation system.

A packed column 19 was used to concentrate the aqueous sodium salts streams from tank 18 containing sodium isobutyrate to about 40–50 wt.% solids. The distillate from column 19 was removed via line 29 and recycled to the isobutyraldehyde feed tank. The bottoms from column 19 provided a concentrated sodium salt medium containing over 30% by weight sodium isobutyrate, which was fed to and combined with the isobutyraldehyde feed via line 14.

The final distillation system first included a ten tray Oldershaw column 23, which was used to dry and remove (via line 28) light from the crude monoester product. The salt concentration in the distillation feed was monitored by use of a specific ion probe for sodium. The crude feed was added to the middle of column 23. The overheads and bottoms temperature were 120–125° and 150° C., respectively. The head pressure was about 20 mmHg. The column 23 bottoms were forwarded to column 24, which was a 5 (five) tray Oldershaw column. The column was fed on the top tray, and the overheads and bottoms temperature were 132–136° and 150–160° C., respectively. The head pressure was about 20 mmHg.

The process was thus run in a continuous fashion from the synthesis static mixer to the final distillation tower. Because of limited throughput of the particular distillation towers used in this work, the residence time of the synthesis static mixer was controlled to balance flows to distillation. The synthesis product exiting the static mixer had a selectivity (diol to monoester) and conversion (100 minus weight percent unreacted isobutyraldehyde) of 12% and 42.4 wt.%, respectively. The yield was 94.8%.

The product stream taken from column 24 overhead via line 25 was analyzed by gas chromatography-mass spectroscopy, GCMS, and the product composition was found to be 0.9 wt.% 2.2.4-trimethyl-1,3-pentanediol, 91.5 Wt.%, 3-hydroxy-2,2,4-trimethylisobutyrate, and 7.3 wt.% 2,2,4-trimethylpentyldiisobutyrate. The monoester recovered in line 25 was produced in a yield of 61.2%. Thus, a product having good quality and yield was produced in a continuous fashion in accordance with the invention.

EXAMPLE 3

Production of Diester and Controlled Coproduction

In this Example, the production of the diester from the monoester, as well as the controlled coproduction of the diester, monoester and diol were demonstrated. A stream weighing 792 grams, and containing 14% isobutyraldehyde, 18% diol, 67% monoester, 0.3% diester and 0.5% sodium isobutyrate salt was fed into a 14 tray Oldershaw distillation column. This mixture was distilled until 55% of the pot charge had been removed. During this distillation, which in this experiment continued over several hours, the bottoms reached a temperature of 162° C. and the tops ranged from 63° to 130° C. It was noted that that after 15% of the pot charge had been removed, the weight% diester in the pot rose sharply, thus indicating rapid formation of the diester. After 30% of the pot had been removed, the diester comprised about 70% by weight of the pot, and upon analysis after about 55% of the pot had been removed the diester comprised about 78% of the product remaining in the pot. At this point, the tops totalled 430 grams, and contained 28% isobutyraldehyde, 51% diol and 20% monoester. The distillation bottoms weighed 362 grams and included 21% monoester, 78% diester and 1% salts. Thus, of the total product (tops and bottoms), approximately 36% was diester, 28% diol and 41% monoester. In another run, the duration and extent of the distillation was increased, and the resulting total product contained 23% diol, 28% monoester and 49% of the diester. Thus, it was demonstrated that this process is highly effective, and can be used to achieve a reaction product highly enriched in the diester, as well as to achieve controlled coproduction of three highly desirable products. Each of these products, of course, can be further purified and isolated using conventional techniques.

What is claimed is:

1. A process for producing 3-hydroxy-2,2,4-trimethylpentyl isobutyrate, comprising the steps of:
    reacting isobutyraldehyde in the presence of an alkali metal hydroxide to produce a reacted medium containing 3-hydroxy-2,2,4-trimethylpentyl isobutyrate and an alkali metal isobutyrate salt;
    separating from said reacted medium, an aqueous medium containing the alkali metal isobutyrate salt;
    removing water from said aqueous medium to concentrate it so as to contain at least about 12.5 weight % of the alkali metal isobutyrate salt; and
    introducing the concentrated alkali metal isobutyrate salt medium into a subsequent one of said reacting steps to increase the reaction rate.

2. A process according to claim 1, wherein said reacting takes place at a temperature of about 60 to about 120° C.

3. A process according to claim 2, wherein said reacting is conducted in a tubular flow reactor.

4. A process according to claim 3, wherein said tubular flow reactor contains a plurality of mixing elements.

5. A process according to claim 3, wherein during said reacting said alkali metal hydroxide is present in an amount of about 0.1 to about 5 mole percent relative to the isobutyraldehyde.

6. A process according to claim 5, wherein said alkali metal hydroxide is sodium hydroxide and said concentrated salt medium is a concentrated sodium isobutyrate medium.

7. A process according to claim 6, wherein said reacting is for a duration of about 0.5 to about 10 minutes.

8. A process according to claim 7, wherein the process is a continuous process in which a first feed stream containing isobutyraldehyde and a second feed stream containing sodium hydroxide are continuously fed into said tubular flow reactor.

9. A process according to claim 8, wherein a third feed stream containing said concentrated sodium isobutyrate medium is also continuously fed into said tubular flow reactor.

10. A process according to claim 9, wherein said tubular flow reactor contains a plurality of mixing elements.

11. A process according to claim 10 in which said concentrated sodium isobutyrate medium is comprised at least about 20 percent by weight of sodium isobutyrate, and said tubular flow reactor contains a plurality of mixing elements.

12. A process according to claim 11 wherein said reacting is at a temperature of about 75 to about 100° C.

13. A process according to claim 12, wherein said reacting is for a duration of about 1 to about 8 minutes.

14. A process according to claim 13, and also including the steps of washing, isolating and recovering said 3-hydroxy-2,2,4-trimethylpentyl isobutyrate.

15. A process according to claim 14, wherein said 3-hydroxy-2,2,4-trimethylpentyl isobutyrate is produced in a molar ratio of at least about 6 to 1 relative to any 2,2,4-trimethyl-1,3-pentanediol produced.

16. A process according to claim 15, wherein said 3-hydroxy-2,2,4-trimethylpentyl isobutyrate is recovered in a yield of at least about 60%.

17. A process according to claim 16, wherein said isolating and recovering includes at least two distillations, and wherein said 3-hydroxy-2,2,4-trimethylpentyl isobutyrate is recovered in a purity of at least about 90%.

18. A process for producing 3-hydroxy-2,2,4-trimethylpentyl isobutyrate, comprising reacting isobutyraldehyde in the presence of about 0.5 to about 5 weight percent, based on the isobutyraldehyde, of an aqueous phase containing at least about 15 weight percent sodium hydroxide and at least about 12.5 weight percent sodium isobutyrate.

19. A process according to claim 18, wherein said reacting is conducted in a tubular flow reactor.

20. A process according to claim 19, wherein said aqueous phase contains at least about 30 weight percent sodium hydroxide.

21. A process according to claim 20, wherein said aqueous phase contains at least about 20 weight percent sodium isobutyrate.

22. A process according to claim 21, wherein said reacting is conducted for a duration of about 0.5 to about 10 minutes.

23. A process according to claim 22, wherein said tubular reactor contains a plurality of mixing elements.

24. A process according to claim 23, wherein said reacting is conducted at a temperature of about 80° to about 90° C.

25. A process according to claim 18, and comprising the further steps of intimately mixing a feed stream containing isobutyraldehyde with:
 about 0.25 to 5 weight percent, based on the isobutyraldehyde, of a feed stream containing at least about 30 weight percent aqueous sodium hydroxide; and
 about 0.1 to 5 weight percent, based on the isobutyraldehyde, of a feed stream containing at least about 20 weight percent aqueous sodium isobutyrate.

26. A process for producing 3-hydroxy-2,2,4-trimethylpentyl isobutyrate, comprising reacting isobutyraldehyde in the presence of an alkali metal isobutyrate salt and an alkali metal hydroxide for a duration of about 0.5 to about 10 minutes.

27. A process according to claim 26, wherein said alkali metal hydroxide is sodium hydroxide and said alkali metal isobutyrate salt is sodium isobutyrate.

28. A process according to claim 27, wherein said reacting is conducted in a tubular flow reactor.

29. A process according to claim 27, wherein said tubular flow reactor contains a plurality of mixing elements and said reacting is at a temperature of about 80° to about 90° C.

30. A process for producing the diisobutyrate ester of 2,2,4-trimethyl-1,3-pentanediol, comprising reacting 3-hydroxy-2,2,4-trimethylpentyl isobutyrate in the presence of an alkali metal isobutyrate for a duration and at a temperature sufficient to obtain a reaction product comprised at least about 10% of the diisobutyrate ester.

31. A process according to claim 30, wherein said reaction product also contains 2,2,4-trimethyl-1,3-pentanediol.

32. A process according to claim 31, wherein the reaction product contains about 10 to 50 weight % of the diester, about 10 to 50 weight T of the diol, and about 10 to 50 weight % of 3-hydroxy-2,2,4-trimethylpentyl isobutyrate.

33. A process according to claim 31, wherein said reacting includes distilling a product of an alkali metal hydroxide-catalyzed condensation of isobutyraldehyde conducted in the presence of an alkali metal isobutyrate, said product containing said 3-hydroxy-2,2,4-trimethylpentyl isobutyrate as well as 2,2,4-trimethyl-1,3-pentanediol and its diisobutyrate ester.

34. A process according to claim 33, wherein said alkali metal isobutyrate is sodium isobutyrate and said alkali metal hydroxide is sodium hydroxide.

* * * * *